United States Patent [19]

Epstein et al.

[11] Patent Number: 5,019,368

[45] Date of Patent: May 28, 1991

[54] DETECTION OF NECROTIC MALIGNANT TISSUE AND ASSOCIATED THERAPY

[75] Inventors: Alan L. Epstein, LaCanada; Clive R. Taylor, S. Pasadena, both of Calif.

[73] Assignee: Cancer Biologics, Inc., Tustin, Calif.

[21] Appl. No.: 314,437

[22] Filed: Feb. 23, 1989

[51] Int. Cl.$^5$ .................. A61K 43/00; A61K 49/02; A61K 39/00; C07K 15/28

[52] U.S. Cl. .......................... 424/1.1; 424/9; 424/85.91; 530/389; 530/387

[58] Field of Search .................. 424/1.1, 85.91, 9; 530/389, 807, 387

[56] References Cited

U.S. PATENT DOCUMENTS

| | | | |
|---|---|---|---|
| 4,331,647 | 5/1982 | Goldenberg | 424/1.1 |
| 4,361,544 | 11/1982 | Goldenberg | 424/1.1 |
| 4,460,559 | 7/1984 | Goldenberg | 424/1.1 |
| 4,460,561 | 7/1984 | Goldenberg | 424/1.1 |
| 4,499,183 | 2/1985 | Sujarsky et al. | 435/6 |
| 4,613,576 | 9/1986 | Cote et al. | 436/548 |
| 4,628,027 | 12/1986 | Gay | 435/7 |
| 4,699,877 | 10/1987 | Cline et al. | 435/6 |
| 4,735,210 | 4/1988 | Goldenberg | 424/1.1 X |
| 4,861,581 | 8/1989 | Epstein et al. | 424/1.1 |

FOREIGN PATENT DOCUMENTS 2067286  7/1981  United Kingdom .................. 424/1.1

OTHER PUBLICATIONS

Chem. Abstracts 107(7):57118b, 1987, S. Welt et al., "Monoclonal Antibody to an Intracellular Antigen . . . " PNAS 84(12), 4200-4204.
Cater et al., Inflammatory Changes in Tumour Vessels .Aafter Systemic 5-Hydroxytryptamine, Bradykinin, Kallikrein, or Lysolecithin. Br. J. Cancer 20:517-525, 1966.
Thomlinson et al., The Histological Structure of Some Human Lung Cancers and the Possible Implications for Radiotherapy, Br. J. Cancer 9:539-549, 1955.
Morgan et al., Monoclonal Antibody Therapy of Cancer: Preclinical Models and Investigations in Humans, In: R. Herberman (ed).
Cancer Immunology: Innovative Approaches to Therapy, pp. 177-200, Boston, Mass: Martinus Nijhoff Publishers, 1986.
Cooper et al., Cell Death in Normal and Malignant Tissues, Adv. Cancer Research, 21:59-120, 1975.
Khaw et al., Myocardial Damage Delineated by Indium-111 Antimyosin Fab and Technetium-99m Pyrophosphate, Science 209-295-297, 1980.
G. G. Steel, "Cell Loss as a Factor in the Growth Rate of Human Tumours", pp. 381-387.
I. F. Tannock, "The Relations Between Cell Proliferation and the Vascular System in a Transplanted Mouse Mammary Tumour," pp. 258-272.
E. H. Cooper, "The Biology of Cell Death in Tumours," Cell Tissue Kinet., pp. 87-95 (1973).
Epstein, A. and Clevenger, C. in Progress in Non-Histone Protein Research, I. Bekhor (Ed.), CRC Press, Boca Raton, 1985, pp. 117-137.
Clevenger, C. and Epstein, A. (1984) Exper. Cell Res. 151, 194-207.
Clevenger, C. and Epstein, A. (1984) J. of Histochem. and Cytochem., 32(7) 757-765.
Beller, G. et al. (1977) Circulation 55(1), 74-78.
Murao, S. et al., (1985) Cancer Res. 45, 791-795.
Bauer, K. et al. (1986) J. of Histochem. and Cytochem. 34(2) 245-250.
Clevenger, C et al. (1985) Cytometry 6, 208-214.
Bauer, K. et al. (1986) Cancer Res. 46, 2428-2434.
Ghose, T. et al. (1975) Europ. J. Cancer 11, 321-326.
Pelham, J. et al. (1983) Cancer Immunol. Immunother. 15, 210-216.
Deguchi, T. et al. (1986) Cancer Res. 46, 3751-3755.
Hurwitz, E. et al. (1975) Cancer Res. 35, 1175-1181.
Marcholonis J. (1969) Biochem. J. 113, 299-305.
Khaw, B. et al. (1976) J. Clin. Invest. 58, 439-446.
Khaw, B. et al. (1979) Circulation 60, 1527-1531.
Centocor: Product Brochure (SNM 1986) "Cardiac Patient Management".
Centocor: Product Brochure (SNM 1986) "Tumor Imaging with Monclonal Antibodies: Ovarian and Breast CA.".
Centocor: Product Brochure (SNM 1986) "Thrombus Detection with Monoclonal Antibodies".

Primary Examiner—Richard D. Lovering
Assistant Examiner—John M. Covert
Attorney, Agent, or Firm—Knobbe, Martens, Olson & Bear

[57] ABSTRACT

Disclosed is a method for enhancing the effects of therapy that kills malignant cells in vivo comprising the steps of obtaining monoclonal antibody that is specific to an internal cellular component of a mammal but not to external cellular components, wherein the monoclonal antibody is attached to an antineoplastic agent; initiating therapy in a mammal to kill malignant cells in vivo, thereby causing some of the malignant cells to become necrotic; and administering the antibodies to the mammal. The antibodies bind to the necrotic malignant cells thereby delivering antineoplastic agent to surrounding cells. Also disclosed is a method of de novo therapy comprising administration of antibody-antineoplastic agent conjugate such that antineoplastic agent is delivered to the tumor. Also disclosed are antibodies for use with the foregoing methods and for use with diagnositc methods.

9 Claims, No Drawings

DETECTION OF NECROTIC MALIGNANT TISSUE AND ASSOCIATED THERAPY

This application is a division of application Ser. No. 938,425, filed Dec. 5, 1986, now U.S. Pat. No. 4,861,581.

BACKGROUND OF THE INVENTION

This invention relates to means for rapidly determining the effectiveness of cancer therapy, and to means for augmenting such therapy through the use of antibodies to necrotic or damaged neoplastic tissue that are conjugated to labels or pharmaceutically active molecules.

Modern techniques for the nonsurgical treatment of cancer include both clinical and experimental techniques involving chemotherapy, radiation therapy, a combination of chemotherapy and radiation therapy, and immunotherapy. In each instance, the object of the therapy is to kill the malignant cells. Antineoplastic agents presently or potentially useful in such therapy include cytotoxic drugs, biological response modifiers, radiosensitizing compounds, toxins, and radionuclides.

One difficulty associated with cancer therapy is that the effectiveness of a particular therapy varies significantly from one type of cancer to another type of cancer, and even among patients with the same type of cancer. In fact, even individual neoplasms in a single patient may be heterogeneous, having some cells that are more receptive or resistant than others to the particular therapy being utilized. For these reasons, the selection of an effective cancer therapy regimen for a particular patient having a particular type of cancer is not an exact science, but must, in the final analysis, be determined empirically.

A. Monitoring of Effects of Therapy

It is the patient that suffers as a result of this lack of certitude in the establishment of the optimal treatment regimen. The side effects from chemotherapy and radiation therapy are notorious, and include weight loss, vomiting, hearing impairment, hair loss, gastrointestinal damage, and bone marrow damage. Accordingly, physicians make every effort to monitor the effects of the particular treatment regimen being utilized. If the treatment is ineffective, it is discontinued and an alternative treatment is instituted as soon as is feasible.

Conventional methods for monitoring the effectiveness of chemotherapy, radiation therapy, and other nonsurgical cancer therapy include CAT scans, liver-spleen scans, X-rays, Magnetic Resonance (MR) scans, and manual palpation of the tumor, all to detect reduction in tumor size. These techniques are generally useful only after three to four weeks of therapy, since a substantial reduction in tumor size is required in order to identify changes. The patient is therefore committed to a particular therapeutic regimen (and concomitant side effects) until completion of these diagnostic methods.

A monitoring technique that would permit the clinician to determine in a short period of time the effectiveness of a particular therapy in each particular patient would greatly facilitate attainment of the optimum therapeutic regimen while minimizing the time required to do so. Such a technique would also permit the treating physician to minimize the time in which the patient is subjected to ineffective therapy with its accompanying side effects.

B. Augmentation Therapy

Because of the heterogeneous nature of many neoplasms, and because of the mechanisms by which certain therapeutic measures work, not all the cells in a tumor respond to therapy. With a heterogeneous neoplasm, some, but not all of the cells may be susceptible to a particular chemotherapeutic agent. Additionally, radiation therapy and antiproliferative chemotherapeutic agents primarily injure only rapidly growing cells. At any one time, the number of cells in a growth phase is likely to represent only a small number of the total cell population in a tumor. For these reasons, such therapy often reduces, but does not eliminate, the tumor burden. Accordingly, there is a need in that situation for an effective method for destroying the remaining tumor cells.

C. De Novo Therapy of Neoplasms

Finally, because of the hetereogeneity of different types of neoplasms, many different therapeutic approaches have been utilized, forcing clinician and patient to undergo extensive and expensive clinical, radiologic, and laboratory investigations to determine the tumor type. There is therefore a clear need to develop therapeutic approaches applicable in a more uniform way to a broad spectrum of different types of cancer.

Antibodies, and in particular monoclonal antibodies, are the focus of intense interest in the field of cancer research. Antibodies have been developed to cell-surface antigens for a number of malignancies, but are useful only in restricted categories of tumors. Techniques are known for conjugating such antibodies to pharmacologically active agents or to labels to permit diagnosis, localization, and therapy directed toward such tumors. Such presently-known conjugates again are useful only in restricted categories of tumors.

Recent research has led to the identification of unique nuclear antigens and the development of monoclonal antibodies thereto. See, e.g., A. Epstein and C. Clevenger, *Identification of Nuclear Antigens in Human Cells by Immunofluorescence, Immunoelectron Microscopy, and Immunobiochemical Methods Using Monoclonal Antibodies*, Progress in Non-Histone Protein Research, 117 et seq. (I. Bekhor ed. 1985); C. Clevenger and A. Epstein, *Identification of a Nuclear Protein Component of Interchromatin Granules Using a Monoclonal Antibody and Immunogold Electron Microscopy*, Exp. Cell Res. 151: 194–207 (1984); and C. Clevenger and A. Epstein, *Use of Immunogold Electron Microscopy and Monoclonal Antibodies in the Identification of Nuclear Substructures*, J. Histochem. and Cytochem. 32: 757–765 (1984). Such antibodies have been labeled and have been used to identify structures within the nucleus. Id.

The cardiac protein myosin is well known. This protein is an intracellular muscle protein found inside cardiac cells, but not on the cell wall. Myosin-specific antibodies have been developed and have been labeled for in vivo imaging of heart tissue damaged by myocardial infarction. See G. Beller, B. Khaw, E. Haber and T. Smith, *Localization of Radiolabeled Cardiac Myosin-specific Antibody in Myocardial Infarcts*, Circulation 55: 74–78 (1977).

BRIEF DESCRIPTION OF THE INVENTION

The present invention exploits the observation that antibodies to insoluble intracellular components of cells can be administered in such a way as to show preferential localization to neoplastic cells in vivo, in spite of the known fact that the relevant antigens also are present in normal cells. Such localization is based upon the demonstrated abnormal permeability of a proportion of cancer cells, as well as the specificity and character of the antibody.

In accordance with one aspect of the present invention, there is provided a method for measuring the effectiveness of therapy intended to kill malignant cells in vivo in a mammal, comprising the steps of obtaining monoclonal antibody that is specific to an internal cellular component of neoplastic and normal cells of the mammal but not to external cellular components, the monoclonal antibody being labeled; contacting the labeled antibody with tissue of a mammal that has received therapy to kill neoplastic cells in vivo; and determining the effectiveness of the therapy by measuring the binding of the labeled antibody to the internal cellular component of the degenerating neoplastic cells.

In one preferred embodiment, the antibody is to an insoluble intracellular antigen, and the contacting step preferably comprises administering the labeled antibody to a mammal in vivo. Preferred labels include radionuclides, magnetic resonance enhancing agents, and radiopaque materials, and preferred methods for measuring the binding of antibody to antigen include imaging techniques including scintigraphic, magnetic resonance, and radiographic imaging.

Another embodiment of the present invention comprises a method for enhancing in a mammal the effects of therapy that kills malignant cells in vivo, comprising the steps of: obtaining an antibody specific to an insoluble internal cellular antigen that is not present on the exterior of a living cell or circulating in the serum, wherein the antibody has conjugated thereto a pharmacologically-active agent, preferably an antineoplastic agent; initiating therapy in the mammal to kill malignant cells in vivo, thereby causing some of the malignant cells to become damaged or necrotic; and administering the antibody conjugate to the mammal whereby the antibodies become bound to the necrotic malignant cells, thereby delivering the pharmacologically-active agent to the locus of those cells. The antineoplastic agent is preferably a cytotoxic agent, a toxin, a biological response modifier, a radiosensitizing compound, an alpha-emitting radionuclide, a beta-emitting radionuclide, or an antiproliferative agent. The therapy used to cause necrosis may advantageously be chemotherapy, radiation therapy, or immunotherapy.

In many malignant neoplasms, both primary tumors and metastases, the pharmacologically-labeled antibody against insoluble intracellular antigens shows preferential localization to the cancerous lesion that is of itself sufficient to cause useful therapeutic killing of neoplastic cells. In this embodiment of the invention, the pharmacologically-labeled antibody to intracellular antigen acts as the primary therapeutic modality and may be used with or without pre-imaging of the tumor using similar antibody linked to imaging isotopes.

Thus, in another embodiment of the present invention, the invention comprises a method for delivering primary or de novo therapy to a wide variety of types of neoplasms, both primary tumors and metastases, to kill the neoplastic cells in vivo, comprising the steps of obtaining an antibody to an insoluble intracellular antigen, wherein the antibody has been selected by screening a library of antibodies that have been generated to insoluble intracellular antigen and selecting those antibodies that are specific to insoluble intracellular antigen present in both neoplastic and normal cells, but not to antigen released into the general circulation upon cell death or to antigen on the exterior of living cells, wherein the antibody has conjugated thereto an antineoplastic agent; and initiating therapy against a neoplasm in a mammal directly by administering the antibody - antineoplastic agent conjugate to a mammal having a neoplasm, whereby the antibody conjugate becomes selectively bound to permeable cells present within primary or metastatic cancers, thereby delivering the antineoplastic agent to surrounding neoplastic cells.

Yet another embodiment of the present invention comprises a monoclonal antibody to an insoluble intracellular antigen, wherein the antibody is bound to an alpha-emitting radionuclide or a beta-emitting radionuclide, or to a chemotherapeutic or immunotherapeutic agent or a biological response modifier.

DETAILED DESCRIPTION OF PREFERRED EMBODIMENTS

Upon cell death and lysis in an animal, soluble components of the cell, primarily from the cytoplasm, are released. The remainder of the necrotic cell comprises a "cell ghost" made up of various generally insoluble materials that remain "fixed" in situ in the tissue. The insoluble cell ghost is gradually destroyed by phagocytosis and enzymatic degradation. At least a portion of the cell ghost remains intact for as long as several weeks. It has been discovered that certain intracellular cell ghost constituents are antigenic. These antigens include nuclear antigens, structural elements, and organelles.

The present invention uses insoluble intracellular antigens for diagnostic and therapeutic purposes, respectively. A diagnostic test in accordance with the present invention utilizes a polyclonal or monoclonal antibody to an insoluble intracellular antigen. The antibody is labeled in a conventional manner. In most instances, the antibodies to insoluble antigens will be labeled with a conventional radiopaque material or a gamma-emitting radionuclide to permit in vivo imaging of localized antibody. The same antibody, linked to a pharmacologically-active agent, may be used for therapeutic purposes.

A. Antibody Preparation

The antibodies used in the present invention may be obtained through conventional polyclonal or monoclonal antibody preparation techniques. Antigen may be obtained from cells of the species toward which the antibodies are to be directed. For antibodies directed toward human intracellular antigens, malignant cell lines represent a convenient source of such antigen.

Insoluble antigen may conveniently be separated through centrifugation techniques. The cell membranes are disrupted by freezing and thawing, by mechanical techniques, or by other suitable methods. Centrifugation at $1000 \times g$ for several minutes is generally sufficient to separate the soluble cytoplasmic fraction from the generally insoluble structural elements and nuclei. Laboratory animals may then be periodically immunized according to accepted procedure to generate the desired immunologic response.

To generate monoclonal antibodies, murine spleen cells from immunized animals are fused with an appropriate myeloma cell line. Fused cells are cultured in selective growth medium, and culture supernatants from active cell cultures are tested for antibody activity. Positive cultures are identified and expanded.

In order to screen for monoclonal antibodies that bind specifically to cell ghosts with little or no binding to live cells, equal aliquots of normal and neoplastic live cells are prepared. To obtain cell ghosts, one aliquot each of neoplastic and normal cells is subjected to several rapid freeze-thaw cycles, and is then washed with buffer to remove soluble components. The ability of monoclonal antibody from each tested culture to bind, respectively, the cell ghosts and the intact cells is then quantitatively measured. One appropriate measurement technique is a radioimmunoassay. Thus, when using murine monoclonal antibody, radiolabeled anti-mouse IgG may be used to quantitate the amount of bound mouse antibody. Direct or indirect immunofluorescence screening techniques may also be used. Specificity for insoluble intracellular antigens may be determined by comparing the amount of antibody bound to cell ghosts with that bound to intact cells.

Antibodies to intracellular antigen identified above are then screened to ensure there is no binding to soluble antigen obtained from necrotic cultures of normal and neoplastic cells by measuring the binding of the antibody in question to the supernatant from those necrotic cultures. Conventional radioimmunoassay techniques may be used.

B. Labels for Antibodies (1) Radiolabels

For imaging purposes, any of the well-known medical radionuclides can be used. Suitable radionuclides include Tc-99 m, I-123, I-125, In-111, In-113 m, Ga-67, or other suitable gamma-emitters.

(2) Radiopaque Materials

Radiopaque materials also may be used to label the antibodies. Suitable radiopaque materials are well known and include iodine compounds, barium compounds, gallium compounds, thallium compounds, and the like. Specific examples of radiopaque materials include barium, diatrizoate, ethiodized oil, gallium citrate, iocarmic acid, iocetamic acid, iodamide, iodipamide, iodoxamic acid, iogulamide, iohexol, iopamidol, iopanoic acid, iprocemic acid, iosefamic acid, ioseric acid, iosulamide meglumine, iosumetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

(3) Magnetic Resonance - Enhancing Materials

Materials that can be detected by or that enhance the effects of magnetic resonance imaging equipment also may be conjugated to the antibodies. Suitable conventional magnetic resonance-enhancing compounds include gadolinium, copper, iron, and chromium. It is preferred that these metal atoms be prepared in the form of a conventional organometallic chelates, which are then bound to the antibody.

C. Therapeutic Agents

A large number of antineoplastic agents are known, many of which can be conjugated to the antibodies of the present invention using known techniques. These antineoplastic agents may include folate inhibitors, pyrimidine analogs, purine analogs, alkylating agents, antibiotics, and radiosensitizing compounds. Specific examples of such antineoplastic agents include acivicin, aclarubicin, acodazole, adriamycin, ametantrone, aminoglutethimide, anthramycin, asparaginase, azacitidine, azetepa, bisantrene, bleomycin, busulfan, cactinomycin, calusterone, caracemide, carboplatin, carmustine, carubicin, chlorambucil, cisplatin, cyclophosphamide, cytarabine, dacarbazine, dactinomycin, daunorubicin, dezaguanine, diaziquone, doxorubicin, epipropidine, etoposide, etoprine, floxuridine, fludarabine, fluoroura-
cil, fluorocitabine, hydroxyurea, iproplatin, leuprolide acetate, lomustine, mechlorethamine, megestrol acetate, melengestrol acetate, mercaptopurine, methotrexate, metoprine, mitocromin, mitogillin, mitomycin, mitosper, mitoxantrone, mycophenolic acid, nocodazole, nogalamycin, oxisuran, peliomycin, pentamustine, porfiromycin, prednimustine, procarbazine hydrochloride, puromycin, pyrazofurin, riboprine, semustine, sparsomycin, spirogermanium, spiromustine, spiroplatin, streptozocin, talisomycin, tegafur, teniposide, teroxirone, thiamiprine, thioguanine, tiazofurin, triciribine phosphate, triethylenemelamine, trimetrexate, uracil mustard, uredepa, vinblastine, vincristine, vindesine, vinepidine, vinrosidine, vinzolidine, zinostatin and zorubicin.

In addition, alpha-emitting and beta-emitting radionuclides may be used. Such compounds include I-131, Yt-99, Cu-67, Au-198, P-32, and other cytotoxic radionuclides.

The antibodies of the present invention also may be conjugated to biological response modifiers, including interleukin-2, vasodilators, any of the interferons, tumor necrosis factor, and the like.

Yet another category of compounds that may be bound to the antibodies of the present invention are toxins such as ricin, tetanus, diptheria, abrin, gelonin, mistletoe, and other materials capable of causing localized necrosis.

D. Conjugation of Labels and Therapeutic Compounds to Antibodies

Numerous techniques suitable for binding various molecules to antibodies have been established. Iodination, for example, may be accomplished using the chloramine-T method described by S. Mills, et al., $^{123}$I-Radiolabeling of Monoclonal Antibodies for In Vivo Procedures, *Hybridoma* 5: 265-275 (1986). This technique may be used to effect iodination to render the antibody radiopaque, or to attach a radionuclide, such as I-125 or I-131.

Other radionuclides may be attached to the antibodies in question through chelation with benzyl EDTA or DPTA conjugation procedures. Still other suitable techniques include the iodogen method disclosed by M. Pimm, et al., In Vivo Localization of Anti-Osteogenic Sarcoma 791T Monoclonal Antibody, *Int. J. Cancer* 30: 75 (1982), and direct iodination with radioactive sodium iodide.

Numerous techniques are available for attaching various molecules, enzymes and proteins to antibodies. For example, many carboxylic acid-containing compounds (such as methotrexate) can be conjugated to immunoglobulins through an active ester intermediate, formed, e.g., by reacting the compound with N-hydroxysuccinimide and dicyclohexylcarbodiimide. See, T. Deguchi, et al., *Effect of Methotrexate-Monoclonal Anti-Prostatic Acid Phosphatase Antibody Conjugate on Human Prostate Tumor, Cancer Res.* 46: 3751-3755 (1986). Others, such as chlorambucil, will bind directly to the antibodies at low pH. See, e.g., T. Ghose, et al., *Immunochemotherapy of Human Malignant Melanoma with Chloroambucil-Carrying Antibody, Europ. J. Cancer* 11: 321-326 (1975).

Amino sugar-containing drugs such as adriamycin and daunomycin may be covalently bound to antibodies by periodate oxidation of the drug, followed by linking of the oxidized drug to the immunoglobulin and subsequent reduction of the product with sodium borohydride. E. Hurwitz, et al., *The Covalent Binding of Dauno-* mycin and Adriamycin to Antibodies, Cancer Res. 35: 1175-1181 (1975).

Conventional techniques also exist for binding biological response modifiers or other proteins to antibodies. Free thiol groups may be introduced into the antibody by reacting antibody with N-succinimidyl-3-(2-pyridyldithio)propionate (SPOP) to introduce 2-pyridyl disulphide groups, which are reduced with dithiotreitol to leave free thiol groups. The protein to be bound to the antibody is incubated with SPDP. Upon mixing the SPDP-modified protein with the antibody containing free thiol groups, the two materials become bound.

Other known techniques, such as the use of dextran T-10 spacers to increase the number of drug moieties linked to antibody molecules can be employed, as can mixed anhydride methods of drug conjugation. The compound 1-ethyl-3-(3-dimethylaminopropyl) carbodiimide hydrochloride (ECDI) may be used to bind amino-containing drugs to the carboxyl groups of antibodies. Alternatively, glutaraldehyde may be used for crosslinking between free amino groups of the antibody and amino groups in the compound to be conjugated thereto.

E. Monitoring and Diagnostic Procedures Using Antibodies to Insoluble Intracellular Antigens One diagnostic or monitoring procedure of the present invention uses labeled antibodies to insoluble intracellular antigens, wherein the label is a gamma-emitting radionuclide of the type previously discussed. This labeled antibody is injected (preferably intravenously) into a patient who has received chemotherapy, radiation therapy, or both. This procedure is preferably carried out at least one or two days after the initiation of the therapy, in order to permit resultant necrosis of the neoplastic tissue to advance to a sufficient point that reasonable numbers of cell ghosts are present. Between 30 minutes and 3 days following administration of the labeled antibody, an appropriate scintigraphic imaging technique is employed to image label localized in necrotic tissue. Suitable imaging techniques include gamma cameras and SPECT (single photon emission computed tomography) techniques.

One alternative imaging technique is radiographic imaging. In this technique, antibody to insoluble intracellular antigen that has been labeled with a radiopaque material is injected a suitable time after initiation of chemotherapy or radiation therapy. After the antibody has localized at the areas of necrotic tissue, radiographic imaging is performed. Other suitable techniques include CAT (computed axial tomography) scans, fluoroscopy and conventional X-ray imaging.

F. Therapeutic Procedures Using Antibodies to Insoluble Intracellular Antigens

By conjugating the antibodies of the present invention to therapeutic, antineoplastic compounds, those therapeutic agents may be delivered directly to the neoplasm, with greatly reduced systemic effect. Two approaches may be employed; first, as augmentation therapy following use of an existing therapeutic modality that may have killed all or part of the tumor; and second, as a primary de novo mode of therapy focusing on the neoplastic cells already showing some degree of abnormal permeability for the therapeutic antibody.

In the augmentation approach, tumor necrosis is initiated by any conventional technique, such as chemotherapy, immunotherapy, radiation therapy, or the like. After initiation of such therapy, necrosis begins and cell ghosts appear in the tumor mass. At this point (usually at least two days after initiation of the primary therapy), a conjugate of an antibody to an insoluble intracellular antigen and a therapeutic compound, preferably an antineoplastic agent, is administered to the patient. Intravenous administration is preferred, although direct injection in the vicinity of the tumor is also contemplated.

Following administration of the antineoplastic agent-antibody conjugate, antibody becomes bound to the cell ghosts in the tumor mass, bringing with it the antineoplastic agent.

If a lethal amount of immunoconjugate is delivered to a necrotic area, healthy, viable tumor cells surrounding this area may be rendered necrotic, enabling additional amounts of immunoconjugate to penetrate the newly necrotic area. In this way, a gangrene-like effect may be possible with destruction of the tumor cells proceeding radially from necrotic to healthy tumor tissue. To achieve this gangrene-like effect, a cytotoxic agent such as a beta-emitting or an alpha-emitting radionuclide may be used.

In the second approach (primary therapy), the method is exactly as described above, except that the need for prior treatment with some other modality (to create an initial population of necrotic cells) is obviated.

The amount of antineoplastic agent-antibody conjugate administered to the patient will vary depending on the antineoplastic agent used and the size of the tumor. However, in general, the dosage is selected to administer a total dose of antineoplastic agent that is equal to or less than the conventional therapeutic dosage of the particular agent selected. It is preferred that the total dosage be between 1% and 50% of the conventional therapeutic dosage, and it is most preferred that the dosage be between 2% and 25% of the conventional therapeutic dosage of the compound. However, as with all cancer therapy, the optimum dosage will be determined by the treating physician based on the individual patient's response to the therapy and the side effects resulting therefrom.

EXAMPLE 1

In order to generate hybridomas producing monoclonal antibody to nuclear antigens, eight human malignant lymphoma and leukemia cell lines were used as a source of antigens. These include the EBV-positive nonproducer Raji and producer AG876 African Burkitt's lymphoma cell lines; the T-cell acute lymphoblastic leukemia CEM cell line; the IgE secreting multiple myeloma U-266 cell line; the erythroleukemia K562 cell line; and the histiocytic type SU-DHL-1 and U-937 and B-cell type SU-DHL-4 diffuse histiocytic lymphoma cell lines. In addition to these cultures, normal peripheral blood lymphocytes pooled from several individuals and separated by the ficoll-hypaque technique were used alone and after four days of stimulation with 5 ug/ml of Pokeweed mitogen. In order to help characterize and screen the monoclonal antibodies, HeLa cells and a normal diploid human fibroblast cell strain established from a skin punch biopsy were used in the immunofluorescence and immunoelectron microscopy experiments. All of the cultures were grown in RPMI-1640 medium (GIBCO) supplemented with 15% fetal calf serum, 100 units/ml Penicillin-G and 100 ug/ml streptomycin sulfate. In order to produce large quantities of cells, 3 liter hanging bar spinner flasks were used after seeding with approximately $4 \times 10^8$ cells. The cells were harvested 4 to 5 days later, washed twice in phosphate buffered saline (PBS), resuspended in 10 ml of buffer A (150 mM NaCl, 20 mM Tris-HCl, pH 8.0, 1 mM EDTA, 1 mM 2-mercaptoethanol, 0.5 mM phenylmethylsulfonylfluoride and 1% aprotinin) containing 10% glycerol, and frozen at $-85°$ C. for future use. Generally, 3 liters of cells yielded 2.5 ml of packed cells per harvest.

In order to obtain nuclear extracts from the human malignant lymphoma and leukemia cell lines and peripheral blood lymphocytes, 2.5 ml of packed cells were thawed and washed once with Ca/pipes buffer (0.01 M $CaCl_2$, $2 \times 10^{-3}$ M piperazine-N, $N^1$-bis (2-ethanesulfonic acid) in a 50-ml centrifuge tube. All procedures were performed at 4° C. and centrifugation was at $1000 \times g$ for 10 minutes. The pellet was then resuspended in 40 ml of Ca/pipes buffer and thoroughly homogenized using a motor-driven polytetrafluoroethylene pestle to disrupt the swollen cells. The nuclei were then pelleted leaving a cloudy supernatant as the cytoplasmic fraction and resuspended in Ca/pipes buffer containing 1% NP-40 (Gallard-Schlesinger). The nuclei were then rehomogenized to remove nuclear membranes and checked by phase-contrast microscopy to be free of contaminating cytoplasmic and membranous debris. Nuclei were then washed twice in Ca/pipes buffer to remove the detergents, resuspended in 8 ml of phosphate-buffered saline, and sonicated three times for 15 seconds at 30-second intervals in order to produce a more homogeneous suspension. The resulting nuclear extracts, which were free of major cytoplasmic proteins, were then frozen in 1-ml aliquots at $-85°$ C. for use in the immunization procedures.

One-milliliter aliquots of the nuclear extracts from each of the eight human lymphoma and leukemia cell lines and the peripheral blood lymphocytes were thawed, resonicated to reduce viscosity, and emulsified in 1.5 ml of complete Freund's adjuvant using two glass syringes and a 20-gauge microemulsifying needle. Three 8-week-old Balb/c female mice per sample were injected subcutaneously at multiple sites using a 22-gauge needle and glass syringe. The mice were reinoculated 2 weeks later as above except the nuclear extracts were prepared in incomplete adjuvant.

The mice received a third inoculation of antigen 10 days later, this time without adjuvant and by intraperitoneal injection. The mice were sacrificed by cervical dislocation 4 days later and the spleens removed using aseptic technique for the hybridoma experiments.

Spleen cells from the sacrificed Balb/c mice were fused with 8-azaguanine resistant mouse myeloma NS-1 cells at a ratio of 5:1, respectively, using 40% polyethylene glycol (PEG) having a molecular weight of 1540. After fusion, the cells were cultured in selective HAT medium containing $10^{-4}$ M hypoxanthine, $4 \times 10^{-7}$ M aminopterin, and $1.5 \times 10^{-5}$ M thymidine in a 96-well microtiter plate at a concentration of $2 \times 10^5$ cells per well. The medium was changed every 3 days and, after the first week, the aminopterin was discontinued. Culture supernatants from wells with active cell growth were tested by indirect immunofluorescence for antibody activity. To help harvest the supernatants, a multichannel pipette was used to transfer the supernatants to other 96-well plates. In order to prevent cross-contamination from well to well, a new sterile pipette tip was used for each supernatant fluid. Positive cultures were transferred to a 24-well cluster plate for expansion and an aliquot of cells was cloned on 0.5% Noble agar containing RPMI-1640 medium, 20% fetal calf serum, and antibiotics. Agar plates were prepared in $60 \times 15$ mm tissue culture petri dishes the day before cloning and were stored at 4° C. until use. In order to assure the growth of an adequate number of colonies, plates were seeded with 500 or 1000 cells in a volume of 50 ul. The cells were then spread on the surface of the agar with a glass rod bent at 90° and the plates were incubated undisturbed for 10 to 12 days in a well-humidified 5% $CO_2$ incubator at 37° C. At this time, a maximum of 24 colonies per hybridoma were picked with Pasteur pipettes and transferred to a 96-well plate for continued growth. Supernatants of these cultures were then retested 4 to 5 days later when the media turned acidic. Positive cultures were then expanded slowly and, when actively growing in tissue culture flasks, they were frozen in liquid nitrogen for safe storage in RPMI-1640 medium containing 20% fetal calf serum, antibiotics and 10% dimethylsulfoxide (DMSO) at a concentration of $5 \times 10^6$ cells per milliliter.

EXAMPLE 2

Antibody for screening was selected from a library of monoclonal antibodies to intracellular antigens that includes the antibodies produced by the hybridomas of Example 1. The selected antibody was screened as follows:

Large cell lymphoma cells (SU-DHL-2) and adenocarcinoma lung cancer cells (A549) were divided into two equal aliquots. One aliquot was washed 2 times with PBS containing 1 mg/ml bovine serum albumin and 0.02% sodium azide (wash buffer) and placed in 4 ml tubes at a concentration of $1 \times 10^6$ cells/tube. The other aliquot was freeze-thawed 3 times rapidly and washed 3 times with wash buffer to remove soluble components. The cell ghosts were then equally divided into the same number of 4 ml tubes as the first aliquots. One tube from each set was then incubated with 1 ml of monoclonal antibody supernatant for 1 hour with continuous shaking at room temperature. The cells were washed 2 times with wash buffer to remove unbound antibody and then incubated with 100,000 cpm of I-125 goat anti-mouse IgG radiolabeled probe to quantitate the amount of bound mouse immunoglobulin. After a 1 hour incubation with continuous shaking at room temperature, the cells were washed 3 times with wash buffer and counted in a gamma counter for 1-minute intervals.

The purpose of this radioimmunoassay was to identify among a subset of antinuclear monoclonal antibodies those reagents which bind specifically to dead cells with little or no binding to live viable cells. A lymphoma cell line and lung cancer cell line were chosen to show that certain antibodies may be used against a wide variety of human tumors to bind and identify dead cells. Three candidate antibodies, 877-8, 898-9 and 899-4, were identified through this limited screening. The results of this procedure are shown in Table 1.

TABLE 1

| Monoclonal Antibody | Data are expressed as counts per minute (CPM) High counts denote antibody binding | | | |
|---|---|---|---|---|
| | SU-DHL-2 | | A549 | |
| | Live Cells | Dead Cells | Live Cells | Dead Cells |
| 244-7 | 5,934 | 6,772 | 3,426 | 5,509 |
| 364-5 | 769 | 622 | 656 | 1,036 |
| 372-2 | 1,592 | 437 | 2,024 | 1,896 |
| 443-4 | 1,211 | 919 | 560 | 1,337 |
| 652-2 | 6,019 | 1,355 | 11,697 | 9,176 |

TABLE 1-continued

| | Data are expressed as counts per minute (CPM) High counts denote antibody binding | | | |
|---|---|---|---|---|
| | SU-DHL-2 | | A549 | |
| Monoclonal Antibody | Live Cells | Dead Cells | Live Cells | Dead Cells |
| 780-3 | 557 | 1,063 | 3,163 | 1,205 |
| 785-5 | 746 | 648 | 1,211 | 2,197 |
| 841-19 | 1,645 | 1,851 | 3,478 | 2,517 |
| 859-4 | 327 | 1,504 | 1,974 | 3,604 |
| *877-8 | 1,481 | 1,833 | 1,641 | 4,680 |
| 891-5 | 1,247 | 2,834 | 2,856 | 5,973 |
| *898-9 | 3,442 | 2,726 | 2,317 | 13,942 |
| *899-4 | 1,980 | 8,193 | 2,232 | 3,534 |
| 1415-1 | 5,550 | 6,158 | 3,821 | 6,363 |
| 1702-5 | 4,711 | 1,786 | 4,696 | 2,666 |
| NS-1 (neg. control) | 552 | 507 | 346 | 738 |

In order to understand the significance of the data in Table 1, it is important to realize that even a "live" in vitro culture will contain a relatively large proportion of necrotic cells, as opposed to a population of similar cells in vivo. Thus, some binding to the "live" cell culture can be expected, even with an antibody that is specific to only insoluble intracellular antigen. It should also be recognized that even though the antibody may not be specific to any surface protein or antigen of the cell line employed in the screening process, certain tumor cell lines (such as histiocytic cell lines) have surface components that exhibit generalized binding of immunoglobulins.

Prior to commencing animal trials, the candidate antibodies identified by the foregoing screening procedure are further screened against normal live and dead cells to confirm that the antibodies are specific to insoluble intracellular antigen found in all cells in the mammal in which the antibodies will be used. Further, the antibodies are screened against the supernatant of necrotic cells to confirm that the antibody does not bind to soluble intracellular antigen.

EXAMPLE 3

Antibody is identified in accordance with the procedure of Example 2 that is specific to insoluble intracellular antigen not present on the cell surface of normal or malignant cells.

In order to reduce the size of the eventual antibody conjugate, purified monoclonal antibody is subjected to pepsin digestion for 20 hours at 37° C. to prepare (Fab')$_2$ fragments. These (Fab')$_2$ fragments are then separated from intact antibody and protein aggregates through Sephadex G-100 (90×2.5 cm) column chromotography. The first protein peak to be eluted contains the (Fab')$_2$ component of the antibody.

The antibody is labeled with I-131 through the method of S. Mills, et al., supra. Using this iodination procedure, an average of at least one or more atoms of I-131 is conjugated to each molecule of monoclonal antibody.

Conventional chemotherapy is initiated for a patient suffering from a solid tumor. Appropriate chemotherapy is administered intravenously. After 24 hours, 1 mg of monoclonal antibody labeled with 10 miCi I-131 is administered intravenously in a 10 ml sterile saline suspension. Six hours laters, the patient is imaged with a gamma camera, which shows strong localized binding of the radiolabeled antibody to the tumor site. The intensity of tumor imaging, when compared with images obtained under identical conditions prior to therapy, is indicative of the degree to which the chemotherapy has resulted in tumor cell death. In addition, it permits visualization of the primary tumor, and localization of metastases of significant size.

Forty-eight hours after the initiation of chemotherapy, chlorambucil antibody conjugate to insoluble intracellular antigen (using the (Fab')$_2$ fragment) is administered intravenously. The antibody-drug conjugate localizes to the cell ghosts of the tumor, delivering the chemotherapeutic alkylating agent to the site of the tumor, with therapeutic effect.

What is claimed is:

1. A method for enhancing in a mammal the effects of therapy that kills malignant cells in vivo, comprising the steps of:

obtaining an antibody specific to an insoluble internal cellular antigen present in degenerating neoplastic cells or cells which may be induced to be permeable that is not present on the exterior of a living cell, wherein said antibody has directly or indirectly bound thereto an antineoplastic agent;

initiating therapy in said mammal to kill malignant cells in vivo, thereby causing some of said malignant cells to become necrotic; and administering said antibodies to said mammal whereby said antibodies become bound to said necrotic malignangt cells, thereby delivering said antineoplastic agent to surrounding cells.

2. A method of claim 1, wherein said antineoplastic agent is selected from the group consisting of a cytotoxic agent, a toxin, a biological response modifier, a radiosensitizing compound, an alpha-emitting radionuclide, a beta-emitting radionuclide, and an antiproliferative agent.

3. The method of claim 1, wherein said cells are killed with radiation.

4. The method of claim 1, wherein said cells are killed with chemotherapy.

5. The method of claim 1, wherein said cells are killed by immunological techniques.

6. A method for delivering primary, de novo therapy to a wide variety of cancer types, both primary tumors and metastases, to kill neoplastic cells in vivo in a mammal, comprising the steps of:

obtaining an antibody specific to an insoluble internal cellular antigen, wherein said antibody is obtained by screening a library of antibodies generated to insoluble intracellular antigens, and selecting those antibodies that are specific to insoluble intracellular antigen present in both neoplastic and normal cells but not present on the exterior of living cells and that is not released into the general circulation upon cell death, wherein said antibody has directly or indirectly bound thereto an antineoplastic agent; and initiating therapy directly by administering said antibody-antineoplastic agent conjugate to said mammal, whereby said antibody conjugate becomes selectively bound to permeable cells present within primary or metastatic neoplasms in said mammal, thereby delivering said antineoplastic agent to cells surrounding said permeable cells.

7. The method of claim 6, wherein said antineoplastic agent is selected from the group consisting of a cytotoxic agent, a toxin, a biological response modifier, a radiosensitizing compound, an alpha-emitting radionuclide, a beta-emitting radionuclide, and an antiproliferative agent.

8. A monoclonal antibody to an insoluble intracellular antigen present in cells which may be induced to be permeable, or in cell ghosts of substantially all neoplastic and normal cells, but not present on the exterior of living cells of said mammal, wherein said antibody is bound to a moiety comprising at least in part an alpha-emitting radionuclide or a beta-emitting radionuclide.

9. A monoclonal antibody to an insoluble intracellular antigen present in cells which may be induced to be permeable, or in cell ghosts of substantially all neoplastic and normal cells of a mammal, but not present on the exterior of living cells of said mammal, wherein said antibody is bound to a moiety comprising at least in part a chemotherapeutic or immunotherapeutic agent or a biological response modifier.

* * * * *